US007071374B2

(12) United States Patent
Zhang et al.

(10) Patent No.: US 7,071,374 B2
(45) Date of Patent: Jul. 4, 2006

(54) METHOD FOR PRODUCING TRIPLOID, SEEDLESS WATERMELON

(75) Inventors: Xingping Zhang, Woodland, CA (US); Tom Vare Williams, Naples, FL (US)

(73) Assignee: Syngenta Participations AG, Basel (CH)

( * ) Notice: Subject to any disclaimer, the term of this patent is extended or adjusted under 35 U.S.C. 154(b) by 118 days.

(21) Appl. No.: 10/349,509

(22) Filed: Jan. 22, 2003

(65) Prior Publication Data

Related U.S. Application Data

(63) Continuation-in-part of application No. 10/091,154, filed on Mar. 5, 2002, now Pat. No. 6,759,576.

(51) Int. Cl.
*A01H 1/00* (2006.01)
*A01H 1/02* (2006.01)

(52) U.S. Cl. .................. 800/266; 800/260; 800/269
(58) Field of Classification Search ............... 800/260, 800/266, 269, 270, 271, 308
See application file for complete search history.

(56) References Cited

U.S. PATENT DOCUMENTS

| 5,007,198 A * | 4/1991 | Gray et al. ................. 800/268 |
| 6,355,865 B1 | 3/2002 | Elmstrom .................. 800/308 |
| 2003/0121075 A1 | 6/2003 | Barham ...................... 800/308 |
| 2003/0163852 A1 | 8/2003 | Barham et al. ............. 800/308 |

FOREIGN PATENT DOCUMENTS

WO   WO 00/70933   11/2000

OTHER PUBLICATIONS

Susin et al. Euphytica 93: 369-373 (1997).*
NeSmith et al. HortScience 36(1): 60-61 (2001).*
Maynard et al. Acta Horticulture 318: 169-178 (1992).*
NeSmith, D.S. and Duval, J.R., *Fruit Set of Triploid Watermelons as a Function of Distance from a Diploid Pollinizer* HortScience, vol. 36(1) (Feb. 2001) pp. 60-61.
Hochmuth, et al., "Cultural Management." in Maynard, D.N., *Watermelons: Characteristics, Production and Marketing* (Virginia, ASHA Press, 2001), pp. 78-97.
United States Department of Agriculture, Insect Pollination of Cultivated Crop Plants, Common Vegetables for Seed & Fruit; Watermelon and Cirton [online]. Originally published 1976 retrieved from the internet: <URL: http://gears.tucson.ars.ag.gov/book/.
Wolf et al., *Genetic Variability in Flower Attractiveness to Honeybees (Apis mellifera L.)within the Genus Citrullus* HortScience, vol. 34(5), (1999) pp. 860-863.
*Known-You Seed*, (Kaohsiung, Taiwan), [catalog], 1991/1992, pp. 22.
*Known-You Seed*, (Kaohsiung, Taiwan), [catalog], 1994, pp. 22.
Crall et al, *SSDL: A High-quality Icebox Watermelon Breeding Line Resistant to Fusarium Wilt and Antracnose* HortScience, vol. 29, No. 6 (Jun., 1994) pp. 707-708.
Maynard et al, *Triploid watermelon production practices and varieties* Acta Horticulture, vol. 318 (1992) pp. 169-178.
Kenny, I.J. and Porter, D.R., *Relative Rind Toughness Among Watermelon Varieties* American Society for Horticultural Science, vol. 38 (1941) pp. 537-540.
Poole, C.F., *Genetics of Cultivated Cucurbits* The Journal of Heredity, vol. 35 (1944), pp. 122-128.
Porter, D.R., *Inheritance of Certain Fruit and Seed Characters in Watermelons* Hilgardia, vol. 12, No. 10 (Jan., 1937) pp. 489-509.

(Continued)

*Primary Examiner*—David H. Kruse
*Assistant Examiner*—Keith O. Robinson
(74) *Attorney, Agent, or Firm*—Edouard G. Lebel; Bruce Vrana (57) ABSTRACT

An enhanced, diploid pollenizer watermelon plant and method used to maximize the yield of triploid seedless watermelons per area. The enhanced pollenizer watermelon plant of the invention is either a hybrid variety, an open-pollinated variety or a synthetic variety, that exhibits the characteristics of small leaves and fruit with a brittle rind that splits when the fruit is overripe or breaks when relatively small physical forces are applied. The watermelon plant of the invention is also preferably characterized by extended flowering duration, thereby increasing the number of triploid watermelon flowers that are pollinated and set fruit. The method for producing a seedless watermelon fruit, includes the steps of providing a pollenizer diploid watermelon plant, extending the duration of flowering of the pollenizer plant while reducing the number of such plants needed to pollenize the same number of triploid watermelon plants, and maximizing dispersal of the pollenizer watermelon plant throughout the field of triploid watermelon plants.

19 Claims, 2 Drawing Sheets

OTHER PUBLICATIONS

Rhodes, B. and Dane, F, *Gene List for Watermelon Cucurbit Genetics Cooperative Report*, vol. 22 (1999) pp. 61-77.

Wagner Force Measurement Instruments, [catalogue] [online]. [Internet: <URL: http://www.wagnerinstruments.com/] retrieved Jan. 13, 2004.

Wagner Force Measurment Instruments, [online manual]. [Internet: <URL: www.wagnerforce.com/manuals/ftmanual.pdf] retrieved Jan. 13, 2004.

Buttrose et al., *Some effects of Light Intensity Day Length and Temperature on Growth of Fruiting and Nonfruiting Watermelon Citrullus-Lanatus Annals of Botany*, vol. 42, No. 179 (1978) pp. 599-608.

Hedge, D.M., *Physiological Analysis of Growth and Yield of Watermelon (Citrullus lanatus Thunb Musf) in Relation to Irrigation and Nitrogen Fertilization Journal of Agronomy & Crop Science*, vol. 160 (1988) pp. 296-302.

Kano et al., *Effects of summer day-time temperature on sugar content in several portions of watermelon fruit (Citrullus lanatus) Journal of Horticultural Science & Biotechnology*, vol. 79, No. 1 (Jan. 2004) pp. 142-145.

Karchi et al., *the importance of cultural practices in materializing yield potential in a tetraploid watermelon cultiver Cucurbit Genetics Cooperative Report*, No. 6 (198) pp. 59-61.

Scott et al., *Calcium Fertilization and Cultiver Affect Watermelon Rind Thickness and Resiliency Hortscience*, vol. 25, No. 9, (1990) pp. 1075.

Sundstrom et al., *Influence of Potassium and Calcium on Quality and Yield of Watermelon Citrullus-Lanatus Cultiver Calhoun-Gray Journal of the American Society for Horticultural Science*, vol. 108, No. 5 (1983) pp. 897-881.

Buttrose et al. *Some effects of Light Intensity Day Length and Temperature on Growth of Fruiting and Nonfruiting Watermelon Citrullus-Lanatus Annals of Botany*, vol. 42, No. 179 (1978) pp. 599-608.

Fan Min et al., *Identification of quantitative trait loci associated with fruit traits in watermelon (Citullus lanantus (Thanb) Mansf) and analysis of their genetic effects Acta Genetica Sinica*, vol. 27, No. 10 (2000) pp. 901-910.

Hegde, D.M., *Physiological Analysis of Growth and Yield of Watermelon (Citrullus lanatus Thunb Musf) in Relation to Irrigation and Nitrogen Fertilization Journal of Agronomy & Crop Science*, vol. 160 (1988) pp. 296-302.

Kano et al., *Effects of summer day-time temperature on sugar content in several portions of watermelon fruit (Citrullus lanatus) Journal of Horticultural Science & Biotechnology*, vol. 79, No. 1 (Jan. 2004) pp. 142-145.

Karchi et al., *The importance of cultural practices in materializing yield potential in a tetraploid watermelon cultivar Cucurbit Genetics Cooperative Report*, No. 6 (198) pp. 59-61.

Scott et al., *Calcium Fertilization and Cultivar Affect Watermelon Rind Thickness and Resiliency Hortscience*, vol. 25, No. 9, (1990) p. 1075.

Sugiyama et al., *Relationship between Rind Hardness and Rind Tissue Structure in Watermelon Journal of Japanese Society for Horticultural Science*, vol. 68, No. 1 (Jan. 1999) pp. 108-116.

Sundstrom et al., *Influence of Potassium and Calcium on Quality and Yield of Watermelon Citrullus-Lanatus Cultivar Calhoun-Gray Journal of the American Society for horticultural science*, vol. 108, No. 5 (1983) pp. 879-881.

* cited by examiner

METHOD FOR PRODUCING TRIPLOID, SEEDLESS WATERMELON

CROSS-REFERENCE TO RELATED APPLICATIONS

This application is a continuation-in-part of U.S. application Ser. No. 10/091,154, filed Mar. 5, 2002, now U.S. Pat. No. 6,759,576. The aforementioned application is incorporated herein by reference in its entirety.

FIELD OF THE INVENTION

This invention is in the field of watermelon breeding, specifically relating to diploid watermelons used to pollinate triploid watermelon plants for the commercial production of seedless watermelon fruit, and includes a novel method for the production of triploid watermelon fruit.

BACKGROUND OF THE INVENTION

Watermelon is an important horticultural crop that accounts for 2% of the world area devoted to vegetable crops. There were 6,024,000 acres of watermelon grown in the world and 187,000 acres of watermelons grown in the United States in 1997 (FAO Production Yearbook 51, 1998). The estimated annual world watermelon value exceeded $7.6 billion when using the United States average price for 1995–1997. The United States watermelon crop amounted to over 41 million cwt, from over 174,000 harvested acres, and a farm value of over $266 million, accounted for 9.2% of the harvested acres, 10.0% of the production, and 3.5% of the value of the United States fresh vegetable industry in 1999 (USDA Agricultural Statistics 2001). California was the leading state in watermelon farm gate value, exceeded $72 million in 2000, due to high percentage of triploid seedless watermelon grown in California. Seedless watermelon receives well above the average price for seeded watermelons in the market.

The goal of plant breeding is to combine in a single variety or hybrid various desirable traits. Desirable traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, and maturity, are important. Other desired traits may include particular nutrient content, color, fruit shape, as well as taste characteristics.

As with many different plants, watermelon contains a fruit part and a plant part. Each part contains different traits that are desired by consumers and/or growers, including such traits as flavor, texture, disease resistance, and appearance traits such as shape and color. The seedless trait in the watermelon fruit is highly desired by consumers. For production of seedless watermelon, optimum pollination characteristics of the pollinating plant are desired.

Seedless watermelon plants are triploid and must be pollinated by the pollen of diploid watermelon plants. To provide adequate pollinization of seedless watermelon plants, it is current practice to plant diploid pollenizer plants over approximately 25–33% of the field surface. The remaining portion of the field is planted with the triploid plants. Thus, to maximize the value of the crop in the field, growers use high yield marketable diploid watermelon varieties, which ultimately compete with the triploid seedless varieties for sun, nutrients, and space.

A pollenizer for seedless watermelon producing small and unmarketable fruits, which are not harvested, has been disclosed (WO00/70933). However, when this pollenizer is used, a lower total yield of marketable fruit is observed when compared to a commercial pollenizer line. Also, the fruits of the pollenizer described in WO00/70933 that are not harvested become hosts for diseases in the future, and their seeds will germinate and grow into weeds, thus reducing future yields.

The present invention recognizes the need to increase the yield of the seedless watermelon, preferably without loss in total yields of marketable fruits. The present invention also recognizes that novel phenotypic characteristics of the diploid pollenizer plants are needed to permit these diploids to be planted in close proximity to the triploid plants and to share the field surface with the triploid plants, thereby effectively decreasing the surface area of the field required for the diploid pollenizers of the invention. The present invention also recognizes the need to minimize the carryover of unharvested pollenizer fruits as weeds into the subsequent season. The present invention also recognizes the need to increase the pollenizing capacity of diploid watermelon plants in order to further decrease the ratio of diploid to triploid plants in the field, thereby also increasing the yield of the seedless watermelon. The present invention also further recognizes the needs to allow farmers to distinguish the seedless fruits from the fruits of the pollenizer in the field and to provide marketable value to the pollenizer fruits themselves.

SUMMARY OF THE INVENTION

The present invention uses a novel diploid watermelon to improve current methods of commercial production of seedless watermelon and to increase seedless watermelon yield. According to the invention, there is provided a novel enhanced, pollenizer diploid watermelon (hereinafter referred to as "enhanced pollenizer") and method for pollinating seedless watermelon plants. The present invention includes an enhanced pollenizer comprising, at maturity, small leaves and bearing brittle fruits. The small leaves allow the enhanced pollenizer to be grown in close proximity to the triploid watermelon plants without competing with them, thereby increasing yields of seedless fruits. The brittleness of the fruit offers the advantage that unharvested fruits of the pollenizer can be easily destroyed through conventional field preparation for minimizing carry over as weeds in future plantings.

The enhanced pollenizer of the present invention preferably further comprises heavily branching lacy vines (also referred to as heavily branched open vines) and therefore preferably comprises a high number of open (lacy) branches. The leaves of the enhanced pollenizer also preferably comprise non-overlapping, deep lobes. The openness of the branched or lacy vine results, in part, from the distinct small and non-overlapping, deep lobed leaves. The lacy branches and the small leaves, preferably with non-overlapping, deep lobes, of the invention have the additional advantage to provide more access of bees to the flowers of both the pollenizing and the triploid plant, thereby enhancing transfer of the pollen from enhanced pollenizer watermelon to the female flowers of the triploid watermelon. Easier access by bees to the male flowers of the enhanced pollenizer and coupled with a greater frequency of male flowers provides a greater pollen source for triploid fruit production.

A second advantage of small leaves, preferably characterized by deep, non-overlapping lobes, is that more sunlight is able to penetrate to adjacent triploid plants. A third advantage of small leaves, preferably characterized by deep, non-overlapping lobes, is that these leaves take up less field area than the substantially larger leaves of the diploid pollenizers currently used in the production of seedless watermelon. Thus, as it is less competitive for light, water and fertilizers, the enhanced pollenizer of the present invention can also be grown closer to the triploid plants, and it does not need dedicated space to grow. When the enhanced pollenizer and method of the present invention are used, the triploid seedless watermelon are preferably grown in solid rows at a standard spacing, the enhanced pollinizer being then inter-planted between the plants within the rows. This results in significantly higher numbers of triploid plants per acre compared to the number of triploid watermelon plants that has traditionally been planted, and higher yields of seedless fruits.

Preferably, the fruit of the enhanced pollenizer of the present invention are small and therefore easier to distinguish from the seedless fruits in the field. Therefore, also according to the present invention, there is provided a novel enhanced pollenizer comprising small fruits with brittle rind. The small fruits with brittle rind also reduce the load to the plant and allow the plant to continue flowering for extended periods of time, significantly greater than pollenizer watermelons that are currently used in the production of seedless watermelon. The longer flowering duration of the enhanced pollenizer, compared to traditional pollenizer diploid watermelons, results in increased fruit set and yield of seedless watermelon. The brittle rind also offers the advantage that unharvested fruits of the pollenizer quickly decompose in the fields, and can be easily eliminated from further re-production through conventional crop disposal (discing and plowing).

An additional advantage of the enhanced pollinizer of the present invention is also that its fruits contain very large amounts of seeds, which can be harvested and sold as edible watermelon seeds for food or feed uses, or for use in medicines. This provides additional value to the grower who can harvest and market the fruits of the enhanced pollenizer as such or its seeds.

The present invention also includes an enhanced pollenizer fruit that weighs approximately in the range of about 2 to 7 lbs, preferably about 2 to about 6 lbs, about 2 to about 5 lbs. The average weight for the fruits of the enhanced pollenizer is preferably about 3.2 lbs.

The present invention further includes an enhanced pollenizer fruit rind that is brittle, breaking under a pressure preferably approximately in the range of about 7 to about 11 lbs/in$^2$ In another preferred embodiment, an enhanced pollenizer fruit rind breaks under a pressure approximately in the range of about 90 to about 150 g/mm$^2$, preferably about 100 to about 148 g/mm$^2$, preferably about 110 to about 145 g/mm$^2$, preferably about 120 to about 140 g/mm$^2$.

The present invention includes an enhanced pollenizer having leaves with a surface area approximately in the range of about 20 to about 70 cm$^2$, preferably about 22.5 to about 50 cm$^2$, preferably about 25 to about 40 cm$^2$. In another preferred embodiment, the average leaf surface area of the leaves of the enhanced pollenizer is approximately about 25 to about 40 cm$^2$, preferably about 27.5 to about 37.5 cm$^2$, preferably about 30 to about 35 cm$^2$.

Also included in the invention is a enhanced pollenizer plant for pollinating triploid plants producing seedless watermelon fruit, comprising, at maturity, the characteristics of smaller leaf size compared to the watermelon variety Sangria™, wherein the fruit rind is more brittle than the rind of the variety Sangria™ (a commercial variety of Syngenta Seeds, Inc.). The enhanced pollenizer preferably further comprises small fruits. The leaves of the enhanced pollenizer preferably comprises deep, non-overlapping lobes.

The pollenizer diploid watermelon of the invention is further enhanced by including resistance to various pests and herbicides via conventional plant breeding methods or genetic transformation.

The present invention also provides a method for inter-planting enhanced pollenizer plants amongst the triploid watermelon plants in a field in a pattern that decreases the ratio of pollenizing plants to triploid plants and increases the field surface for triploid plants. This allows for a higher population of triploid plants, than conventional practices, and results in 25–33% higher yield of seedless fruits.

Also included in the present invention is a method of increasing the yield of triploid, seedless watermelon comprising the steps of reducing fruit load of said enhanced pollenizer watermelon, increasing the flowering duration of said pollenizer watermelon, planting said enhanced pollenizer watermelon in a field of triploid watermelon; and harvesting said triploid watermelon.

The invention also provides a method of increasing the yield of triploid seedless watermelon plants by using enhanced pollenizer watermelon plants, preferably with small fruits, wherein the fruit as such are not harvested for human consumption. Preferably, the seeds of the fruits of the enhanced pollenizer are used as food or feed, or in medicines.

The present invention also provides a method for producing an enhanced pollenizer comprising crossing a first watermelon plant having small leaves with a second watermelon plant producing fruit with brittle rind that splits easily and selecting for a watermelon plant having the characteristics of the enhanced pollenizer disclosed herein. Preferably, the first watermelon plant further comprises the characteristic of a heavily branching lacy vine. Preferably, the leaves of the enhanced pollenizer preferably comprises deep, non-overlapping lobes. Preferably, the first watermelon plant has the characteristics of OW824 disclosed herein. Preferably, the second watermelon plant bears small fruit. Preferably, the second watermelon plant has the characteristics of OW823 disclosed herein. In a preferred embodiment, the first watermelon plant is OW824. In a preferred embodiment, the second watermelon plant is OW823. In another preferred embodiment, the first watermelon plant is OW824 and the second watermelon plant is OW823. The method preferably further comprises fixing the traits of the enhanced pollenizer.

The present invention also discloses a watermelon enhanced pollenizer obtainable by a method comprising the steps of a) crossing a watermelon plant with a plant of NO1F3203B deposited under Accession No. PTA-4856, b) obtaining a progeny, c) selecting said progeny for the characteristics of the enhanced pollenizer, preferably small leaves and brittle fruit, In a preferred embodiment, it is further selected for heavily branching lacy vines, preferably for small fruit. In a preferred embodiment, the method further comprises crossing said progeny either with itself or with a plant of NO1F3203B, or with another enhanced pollenizer, and selecting for the said characteristics of the enhanced pollenizer. The method preferably further comprises fixing the traits of the enhanced pollenizer.

DETAILED DESCRIPTION OF THE INVENTION

Development of Seedless Watermelons

Triploid watermelons are created by crossing a tetraploid (4X) female parent line with diploid (2X) male parent line. The resulting triploid (3X) watermelon seeds are planted in a field with diploid watermelon pollenizers. The resulting fruit of the triploid watermelon are seedless.

To create a tetraploid female watermelon line, it is known in the art to use chemicals that alter mitosis of a diploid inbred line so that unusual numbers of chromosomes are obtained. For example, colchicine is a chemical that alters the mitotic spindle fibers of diploid cells resulting in a number of cells that are tetraploid. The diploid line used to create a tetraploid is selected based on the traits desired for the tetraploid line. Traits that are desired for a tetraploid line may therefore first be introgressed into the diploid inbred lines that will be used to develop the tetraploid lines by breeding methods well known to those skilled in the art. Thus, the diploid and tetraploid parent lines are bred separately for the desired traits.

It usually requires at least two generations of self-pollination and selection to "fix" the 4X condition, after the colchicine treatment generation because, often, chromosomal aberrations are encountered that affect seed fertility, and must be eliminated. Once the stable tetraploid containing the desired characteristics is verified, it then can be used as a stable female parent for the production of the triploid hybrid. A stable diploid inbred is selected for use as the male parent. Methods for developing tetraploid plants are described in Kihara, H., 1951, Triploid Watermelons, *Proceedings of American Society for Horticultural Science* 58:217–230; and Eigsti, O. J., 1971, Seedless Triploids, HortScience 6, pgs. 1–2.

The tetraploid female parent line and diploid male parent line are planted in a seed production field. The pollen of the diploid male parent is transferred to the female tetraploid flower by methods well known to those skilled in the art. The triploid seed that is produced is present in the resulting fruit and is planted to produce the triploid plants. The breeding of watermelon is further described in Mark Bassett (Editor), 1986, Breeding Vegetable Crops, AVI Publishing, ISBN 0-87055-499-9.

A triploid seedless watermelon is a true F1 hybrid between a tetraploid watermelon, as the female parent, and a diploid watermelon, as the male parent (Kihara, H. 1951. Triploid Watermelons. *Proceedings of American Society for Horticultural Science* 58:217–230). The seedless condition in triploid watermelon is the result of the presence of three homologous sets of chromosomes per somatic cell rather than the usual two. Cells with three sets of homologous chromosomes are said to be triploid and are designated as 3X. The triploid seedless watermelons have 33 chromosomes (2N=3X=33) in their somatic cells. The inability of the triploid zygote to produce normal viable gametes (pollen and egg cells) causes the absence of seeds in triploid fruits. Typically, seedless watermelons contain small edible white ovules, similar to those in immature cucumbers.

Adequate viable pollen supply from the diploid pollenizer watermelon is essential for the triploid female flowers to set and develop into regular seedless fruit. The female flowers of triploid watermelon will not set if they are not pollinated by viable pollen of diploid watermelon. (Maynard, D. N. (editor), 2001, *Watermelons: Characteristics, Production and Marketing*, ASHS Press, ISBN 0-9707546-1-2). The diploid watermelon grown in a field of triploid plants is referred to herein as the "pollenizer." In current commercial triploid watermelon production fields, the triploid watermelon and diploid pollenizer are inter-planted, either within row or between rows, in a ratio of approximately 1 diploid to 2 or 3 triploids. Although research has indicated a 1:4 ratio is acceptable, it is rarely used in commercial plots. (Ne-Smith, D. S., Duval, J. R. *Fruit Set of Triploid Watermelons as a Function of Distance from a Diploid Pollenizer*, HortScience 36(1): 60–61, 2001)

Development of Enhanced Pollenizer Diploid Watermelon

According to the present invention, a watermelon (OW824) is selected having the characteristics of a heavily branching lacy vine, early and prolific male flowers, and small leaves with deep, non-overlapping leaf lobes. In this example, the fruit of OW824 is relatively large, the rind and flesh are very firm, the seed size is very big and the flesh is white. OW824 is a publicly available edible seed watermelon variety generally referred to as XinJiang edible seed watermelon.

Also according to the invention, a hybrid watermelon (OW823) is selected for its small fruit (2–3 kg) with brittle rind that splits easily. OW823 also includes the characteristics of mid-sized seeds with yellow flesh and has relatively large leaves. OW823 is a commercially available variety, Tiny Orchid, from Known-You Seeds, Ltd. of Taiwan.

Crossing OW824×OW823 generated progeny having the characteristics of the enhanced pollenizer diploid watermelon of the present invention as described in more detail below.

The initial cross of OW824×OW823 was made during the summer of 2000 in California. The $F_1$ generation was grown in the greenhouse in the fall of 2000. The $F_2$ population was grown Florida in the spring, and in California in the summer of 2001. Individuals with the set of traits required for the enhanced pollenizer were successfully identified and self-pollinated in $F_2$ populations grown in both locations. A total 7 selections were made. The 7 $F_3$ lines were grown in the field in Florida and the greenhouse in California in the fall of 2001 for further selection and evaluation. Three $F_3$ lines were identified to best meet our breeding goals and advanced to $F_4$ generation. They all have the set of the traits required by the enhanced pollenizer. One line, NO1F3203B, now called SP1, is fixed for every trait concerned. NO1F3203B contains the traits that are illustrative of the traits of the enhanced pollenizer of the invention. Other enhanced pollenizer lines with similar characteristics were for example SP2 with slightly larger leaves than SP1, and SP3 with slightly larger fruits than SP1 and a different fruit skin color.

Leaf: The leaves of the enhanced pollenizer are significantly smaller and are more numerous than that of the commonly used pollenizers such as the variety Sangria™ (See FIGS. 1 and 2). The leaves of the enhanced pollenizer preferably have a surface area approximately in the range of about 20 to about 70 $cm^2$, preferably about 22.5 to about 50 $cm^2$, preferably about 25 to about 40 $cm^2$. In another preferred embodiment, the average leaf surface area of the leaves of the enhanced pollenizer is approximately about 25 to about 40 cm$^2$, preferably about 27.5 to about 37.5 cm$^2$, preferably about 30 to about 35 cm$^2$. The leaves of the enhanced pollenizer preferably have deep, non-overlapping leaf lobes.

The leaf surface areas of the enhanced pollenizer NO1F3203B and the Sangria™, a pollenizer favored by growers, are shown for comparison purposes in Table 1. The leaves for both NO1F3203B and Sangria™ were taken from mature plants sowed on Aug. 20, 2001 and harvested on Nov. 8, 2001.

TABLE 1

| NO1F3203B LEAF | cm$^2$ | SANGRIA LEAF | cm$^2$ |
|---|---|---|---|
| A | 38.75 | A | 232.00 |
| B | 26.25 | B | 447.25 |
| C | 39.75 | C | 241.50 |
| D | 28.75 | D | 238.00 |
| E | 38.25 | E | 211.00 |
| F | 26.27 | | 273.95 (±97.60) |
| | 33.08 (±6.46) | | |

The surface area of the enhanced pollenizer leaf of the invention is approximately 5 to 12 times less than the surface area of the typical diploid pollenizer, Sangria™ plant.

Figure 1:
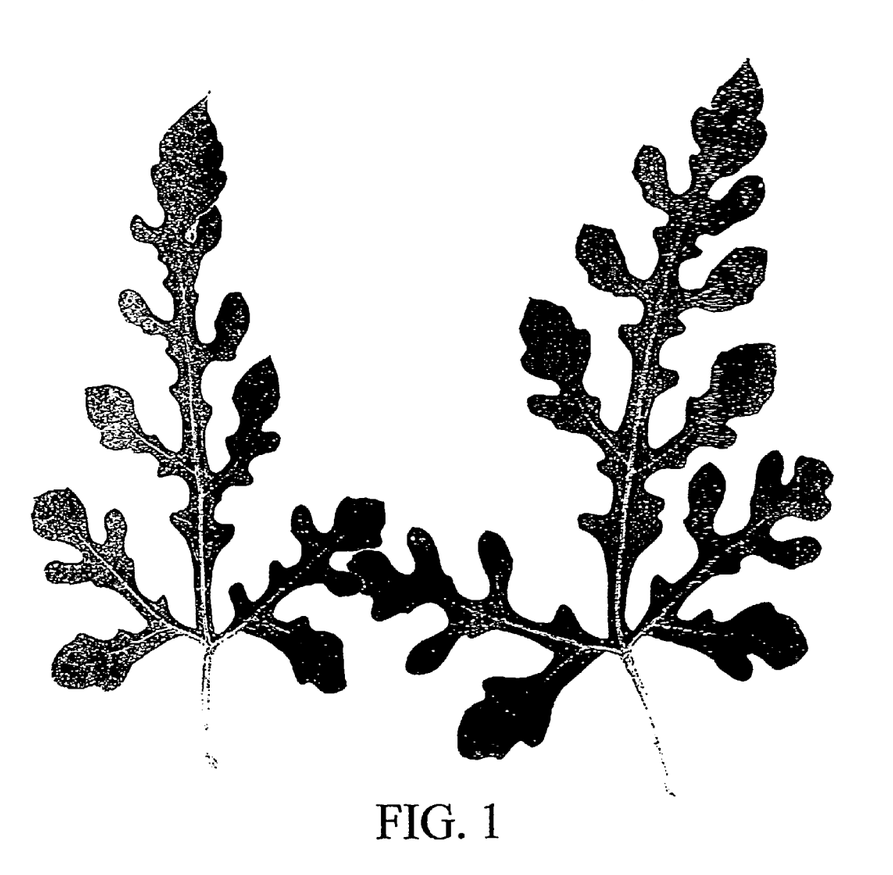
FIG. 1 is a photographic depiction of a leaf of the enhanced pollenizer plant of the invention.
Figure 2:
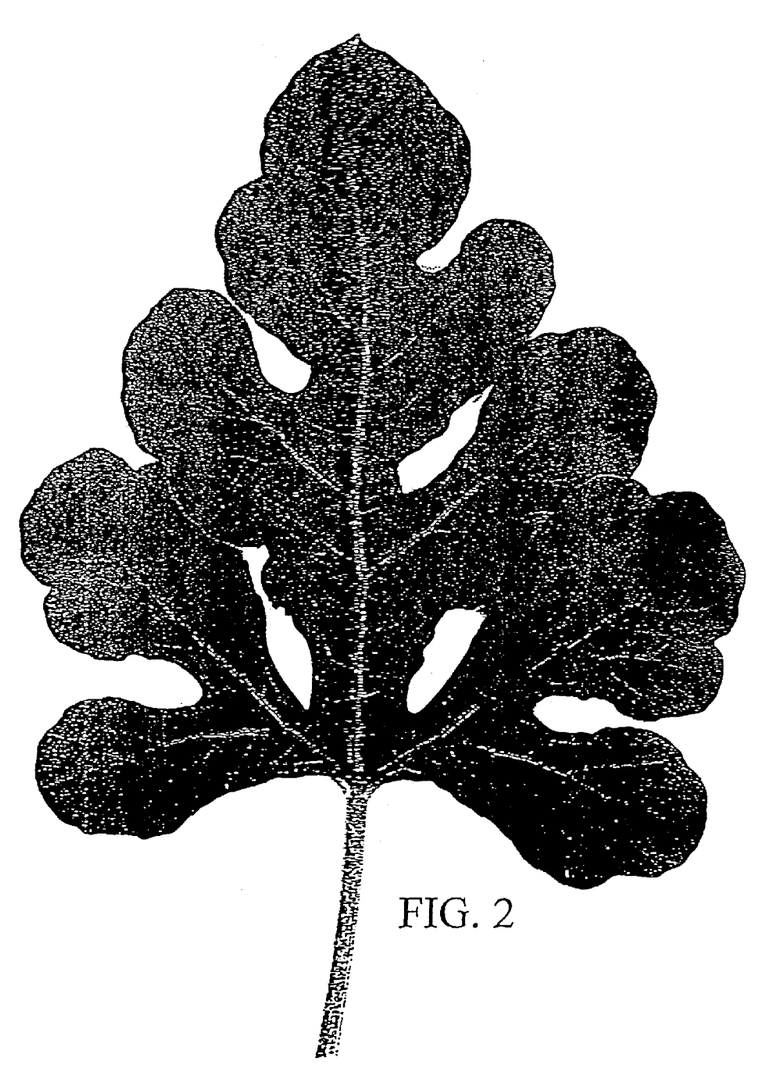
FIG. 2 is a photographic depiction of a leaf of the pollenizer referred to as Sangria™ that is currently used in commerce.

FIG. 1 illustrates the non-overlapping characteristic of the deep, non-overlapping lobed leaves of the enhanced pollenizer. Clearly, due to various environmental and physical forces, some of the leaves in this population may have some overlapping lobes, but overlapping lobes are not characteristic thereof. In contrast, the Sangria™ leaf shown in FIG. 2 is characterized as having leaf lobes that habitually overlap each other. The small, deeply lobed and non-overlapping leaves of the invention allow more sunlight through to adjacent triploid watermelon plants.

Branching: The enhanced pollenizer of the invention is preferably also heavily branched (also referred to as "lacy vined" or "open vines"), having significantly more branches (average of 25.9) than the variety referred to as Sangria™, (average of 13). The lacy vine characteristic enables the enhanced pollenizer to produce more accessible male flowers than current diploid pollenizers, thereby enhancing exposure of the flowers to bees. The open or lacy vines also permit the interplanting of the enhanced pollenizer between triploid plants thereby allowing for higher triploid populations and greater seedless fruit production.

Fruit: The fruit rind of the enhanced pollenizer is very brittle and is easily broken. The brittle fruit rind splits easily, due to natural maturation or by breaking or splitting of the fruit during harvest of the seedless triploid watermelon (for example from foot traffic). Splitting of fruit signals the plant that it hasn't completed its reproductive process inducing the plant to continue flowering for a longer period of time. Brittleness is conferred by a gene e (explosive rind, thin, and tender rind, bursting when cut (Rhodes & Dane, 1999, *Gene List for Watermelon*, Cucurbit Genetics Cooperative Report 22:71–77). When measured by a penetrometer, the NO1F3203B breaks at about 7–11 lbs/in$^2$, whereas a typical watermelon such as Sangria™ breaks at about 21–27 lbs/in$^2$. Using a Tester FT02 of Wagner Instruments, Greenwich, Conn. 06836, the fruit of the enhanced pollenizer preferably breaks under a pressure approximately in the range of about 90 to about 150 g/mm$^2$, preferably about 100 to about 148 g/mm$^2$, preferably about 110 to about 145 g/mm$^2$, preferably about 120 to about 140 g/mm$^2$. By comparison, the fruit of Sangria™ breaks under a pressure of approximately about 300 g/mm$^2$.

Preferably, the fruit size of the enhanced pollenizer is approximately in the range of about 5 to about 7 inches long×about 6 to about 8 inches wide. Preferably, the fruit size of the enhanced pollenizer is approximately about 6 inches long×about 7 inches wide, whereas the typical pollenizer is about 10 inches long×20 inches wide. Small fruit size, as well its brittleness was selected to decrease the load on the plant, thereby extending the duration of plant growth and flower production. Another advantage of the small fruit size is that it enables the harvester to easily distinguish the seedless fruit from seeded fruit, is often difficult with currently used pollenizers, which are selected based on their overall similarity to the seedless triploid plants. The fruit of the enhanced pollenizer weighs approximately in the range of about 2 to about 7 lbs, preferably about 2 to about 6 lbs, preferably about 2 to about 5 lbs. The average weight for the fruits of the enhanced pollenizer is preferably about 3.2 lbs.

The rind color of the enhanced pollenizer is preferably light green with very thin dark green lines. The fruit of the enhanced pollenizer of the invention can be distinguished from the fruit of most (about 99%) of the commercially available seedless watermelon varieties.

Flowering: The plants of the enhanced pollenizer, e.g. of NO1F3203B, also flower approximately 7 to 10 days earlier than diploid pollenizer plants currently used for the production of seedless watermelon, and continue flowering during fruit harvest time of the seedless watermelon, 2 to 3 weeks longer than standard diploid pollenizer plants. Thus, the pollenizer plant of the invention has a flowering duration that is approximately 3 to 5 weeks longer than pollenizers currently used.

Other Traits: The enhanced pollenizer, e.g. NO1F3203B, can be used either as donor of the set of traits disclosed above, or as the recurrent parent to develop additional enhanced pollenizer lines. In accordance with the invention, the enhanced pollenizer watermelon contains traits of disease resistance (e.g. Fusarium wilt, Anthracnose, Gummy Stem Blight, Powdery Mildew, and Bacterial Fruit Blotch), insect resistance (e.g. cucumber beetle, aphids, white flies and mites), salt tolerance, cold tolerance and/or herbicide resistance added. These traits can be added to existing lines by using either conventional backcrossing method, pedigree breeding method or genetic transformation. The methods of conventional watermelon breeding are taught in several reference books, e.g. Maynard, D. N. (editor), 2001, WATERMELONS Characteristics, Production and Marketing, ASHS Press; Mohr, H. C., Watermelon Breeding, in Mark J. Bassett (editor), 1986, Breeding Vegetable Crops, AVI Publishing Company, Inc. General methods of genetic transformation can be learned from publish references, e.g. Glich et al., (Eds), 1993, Methods in Plant Molecular Biology & Biotechnology, CRC Press, and more specifically for watermelon in WO02/14523.

Forms of the Enhanced Diploid Pollenizer: Once the enhanced pollenizer lines are developed, several forms of enhanced pollenizer varieties can be used in commercial seedless watermelon production. Specifically, these forms of enhanced pollenizer varieties include: Forms of Enhanced Pollenizer: (1) Open Pollinated Variety: The stable, enhanced lines of the enhanced pollenizer are grown in isolated fields, at least 2,000 meters from other watermelon varieties. Pollination is conducted in the open fields by bees. Seeds are harvested from the seed production field when the fruit and seeds are fully developed. The seeds are dried and processed according to the regular watermelon seed handling procedures. (2) Synthetic Variety: The seed of different enhanced pollenizer lines are individually produced in isolated fields. Bee pollination is used in each isolation. The seed of different enhanced pollenizer are separately harvested and processed. Mixing several enhanced pollenizer lines in various ratios forms the synthetic varieties. The synthetic variety can provide a broader pollenizer population for the triploid watermelons. (3) Open-Pollinated Hybrid Variety: Two or several enhanced pollenizer lines are planted in the same seed production field with bee pollination. The harvested seed lot, therefore, contains both hybrid and inbred seed. (4) Hybrid Variety: Two enhanced pollenizer lines, the male and female parents, are planted in the same field. Hand pollination is conducted. Only the seed from female parent line is harvested and sold to the commercial grower to use as pollenizer. Table 3 in Example 7 shows the results obtained using various combinations of inbred and hybrid enhanced pollenizers.

Method of Seedless Watermelon Production: Most current commercial seedless watermelon growers in NAFTA use elongated diploid varieties with an Allsweet stripe pattern: light green skin with wide green stripes, as the pollenizer. The variety referred to as Sangria™ is the most preferred Allsweet type pollenizer and is available as a commercial product from Syngenta Seeds, Inc., Boise Id. Typically, the pollenizer is inter-planted with the triploid watermelon either between rows or within row. The current method of planting diploid pollenizers include planting the diploid plants at a distance from adjacent triploid such that they have the same field area available per plant as the field area that is available to the triploid watermelon plants. For example, currently watermelon growers inter-plant the diploids within a row, whereby the space between all adjacent plants within the row are approximately equidistant.

Alternatively, diploid pollenizer plants are planted in separate rows between rows of triploid watermelon plants. All rows of diploid and triploid plants in such a field are planted approximately equidistant from each other. In other words, under current methods for producing seedless watermelon, the width of all diploid and triploid rows is the same.

The method of the present invention includes planting the enhanced pollenizer watermelon plants in rows that are narrower than the triploid rows, thereby saving field area for production of triploid seedless watermelon.

Table 2 below shows different planting alternatives for watermelon pollenizer, including a preferred interplanting according to the present invention (right column).

TABLE 2

| seeded | seedless | seedless | seeded | seedless | seedless | seeded |
|---|---|---|---|---|---|---|
| Conventional 2:1 pollenizer ratio using the row method ||||||||
| O | X | X | O | X | X | O |
| O | X | X | O | X | X | O |
| O | X | X | O | X | X | O |
| O | X | X | O | X | X | O |
| O | X | X | O | X | X | O |
| O | X | X | O | X | X | O |
| O | X | X | O | X | X | O |
| Conventional 2:1 pollenizer ratio using the within row method ||||||||
| X | O | X | X | O | X | X |
| O | X | X | O | X | X | O |
| X | X | O | X | X | O | X |
| X | O | X | X | O | X | X |
| O | X | X | O | X | X | O |

TABLE 2-continued

| seeded | seedless | seedless | seeded | seedless | seedless | seeded |
|---|---|---|---|---|---|---|
| X | X | O | X | X | O | X |
| X | O | X | X | O | X | X |
| O | X | X | O | X | X | O |
| Pollenizer inter-planted at a 3:1 pollenizer ratio ||||||||
| X | X | X | X | X | X | X |
|   | ♦ |   |   |   | ♦ |   |
| X | X | X | X | X | X | X |
| ♦ |   |   | ♦ |   |   | ♦ |
| X | X | X | X | X | X | X |
|   |   | ♦ |   | ♦ |   |   |
| X | X | X | X | X | X | X |
|   |   |   | ♦ |   |   |   |
| X | X | X | X | X | X | X |
| ♦ |   |   | ♦ |   |   | ♦ |
| X | X | X | X | X | X | X |
|   | ♦ |   |   | ♦ |   |   |
| X | X | X | X | X | X | X |
|   |   | ♦ |   | ♦ |   |   |
| X | X | X | X | X | X | X |

Seeded = O
Seedless = X
Pollenizer = ♦

EXAMPLES

The following Examples are provided to illustrate the present invention, and should not be construed as limiting thereof.

Example 1

Triploid watermelon plants are planted in parallel rows 7 feet apart and 3 feet apart within each row. However, the enhanced diploid watermelon plants are planted in a narrow row 3.5° wide (½ the width of the triploid rows) between every second and third triploid row. For example, rows A and B are two consecutive rows of triploids, each 7-foot wide. Row C is a diploid row that is 3.5 feet wide. Row D and E are the following two 7 foot wide rows of triploids, followed by the 3.5-foot wide row F of diploid plants. This pattern is repeated across the width of the field. Because the diploid row is narrower according to the method of the invention, the distance between rows B and D is 10.5 feet instead of the traditional distance of 14 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

Example 2

Triploid watermelon plants are again planted in parallel rows 7 feet apart and 3 feet apart within each row. As in Example 1, the enhanced diploid watermelon plants are planted in a narrow row 3.5° wide, but are planted between every third and fourth triploid row. For example, rows A, B, and C, are three consecutive rows of triploids, each row being 7' wide. The following row D is a diploid, row that is 3.5 feet wide. Row E, F, and G are the following three rows of triploids, all 7 feet wide, followed by a 3.5 foot wide row of enhanced pollenizer plants. This pattern is repeated across the width of the field. Because the diploid row is narrower according to the method of the invention, the distance between rows B and D is again 10.5 feet instead of the traditional distance of 14 feet. Using this ratio of 1 pollenizer row for every 3 triploid rows (1:3), 25% of the field would normally be used for the pollenizer plants. Reducing the width of the pollenizer row according to the method of the invention by one-half, the gain of space for planting additional triploid plants would be 25%/2 or approximately 12%.

Example 3

Triploid watermelons are planted in parallel rows 8 feet apart and 3 feet apart within each row. The enhanced diploid watermelon plants are planted in a narrow row 4.0 feet wide (½ the width of the triploid rows) between every second and third triploid row. For example, rows A and B are two consecutive rows of triploids, each 8 foot wide. Row C is a diploid row that is 4.0 feet wide. Row D and E are the following two 8 foot wide rows of triploids, followed by the 4.0 foot wide row F of diploid plants. This pattern is repeated across the width of the field. Because the diploid row is narrower according to the method of the invention, the distance between rows B and D is 12.0 feet instead of the traditional distance of 16 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

Example 4

Referring to the above three examples, when triploids are planted in rows 8 feet apart, and the ratio of diploid to triploid is 1:3, it is now clear that the reduction of the pollenizer row width by one-half will gain space for planting additional 12%.

Example 5

It is also within the scope of the invention to reduce the pollenizer row width to approximately ⅓ that of the triploid row width. Thus, according to the present invention, at any row width, when the ratio of diploid rows to triploid rows is:
  (a.) 1:2, the savings of field area for additional triploid plants is (33%×⅔) or 22%.
  (b) 1:3, the savings of field area for additional triploid plants is (25%×⅔) or 16.5%.
  (c) 1:4, the savings of field area for additional triploid plants is (20%×⅔) or 13.2%.
It is also within the scope of the invention to reduce the pollenizer row width to approximately ⅔ that of the triploid row width.

Example 6

It is also within the scope of the present invention to inter-plant the diploid plants within the rows of triploid plants. According to the invention, the triploid plants are first planted by machine or by hand in regularly spaced rows. The triploid plants within each row are planted, for example, 3 feet apart. After the triploid plants are in the field as described, the diploid pollenizer watermelon plants of the invention are inter-planted, by hand, within each row approximately midway between the triploid plants. Thus, in this example, the diploid plants are planted approximately 1.5 feet from the flanking triploid plants within the row. Due to the characteristics of the enhanced pollenizer of the invention, the diploid plants can be inter-planted within each row after every 2, 3, 4, 5, 6, 7, 8, 9, or 10 consecutive triploid plants. It is currently preferred in the industry to plant the diploid plants after every 2 (1:2) or 3 (1:3) triploid plants within the row. A 1:4 ratio has been reported, but is not normally used in commercial fields due to inadequate pollenization of the triploid plants. The field area saved under this example, when compared with both the current methods of planting diploids in separate rows or within a row at the ratios (diploid:triploid) of:
  (a) 1:2, is 33.3%,
  (b) 1:3, is 25%,
  (c) 1:4, is 20%.

The enhanced pollenizer and method of the present invention comprises planting the enhanced pollenizer watermelons in rows that are narrower than the rows containing the triploid plants. Although the narrower diploid row will encourage diploid plant growth into the triploid plant row, the novel characteristics of the enhanced pollenizer watermelon allow it maintain its ability to sufficiently pollinate the triploid plants in the field. Thus, the enhanced pollenizer watermelon and method of the present invention increase the yield of seedless watermelon in a field.

Example 7

A split-plot design is used for this experiment to test three inbred enhanced pollenizers and three hybrid enhanced pollenizers against the commercial checks Sangria 2:1 and Sangria 3:1. All 6 enhanced pollenizers are inserted between regularly spaced (80"×24") triploid plants in the ratio of 3:1. For Sangria 2:1 ratio, every third space is a Sangria plant. For Sangria 3:1 ratio, every $4^{th}$ space is a Sangria plant. A 5:1 ratio is also included in this trial using the mixed enhanced pollenizers. In this treatment, the enhanced pollenizers plant is inserted between $5^{th}$ and $6^{th}$ regularly spaced triploid plants. So there are total 9 main plots, the 9 main treatments/pollinators, in this experiment. The 9 main plots are separated by cantaloupe plants. 3 different triploids, the sub-plots, with 2 replications are used to test different pollinators (see table 3). Plants are well grown except the leaf-miner damage. This damage results in smaller fruit size for Palomar and Tri-X-313. The trials are evaluated after about two months. The number of triploid fruit in each sub-plot is counted. The first 15 fruits in each sub-plot are non-selectively harvested and weighted. 10 fruits are also harvested from each pollinator and measured for rind firmness. Data are analyzed using S-Plus 6.1. The enhanced pollenizers varieties are also evaluated for fruit size and other fruit characteristics.

As shown in table 3, very similar fruit set per plant is achieved for all the pollenizer used. Smaller triploid seedless melons are produced when Sangria is used as pollinator in the ratio of 2:1 in this experiment. This could be due to Sangria's strong competition to the triploid plant for space, water and nutrient. A lot more seedless melons per acre, 25%

(compared to the 3:1 ratio) to 33% (compared to the standard 2:1 ratio), are produced when enhanced pollenizers varieties are used as pollenizer.

The rind of enhanced pollenizer varieties of the present invention is much less durable compared to diploid pollenizer Sangria, as indicated by the force used to penetrate the rind using a fruit firmness tester (Fruit Firmness Tester FT02 of Wagner Instruments, Greenwich, Conn. 06836). Should the pollenizer not be harvested for its commercial value, its brittle rind allows the pollinator fruit to be destroyed during fruit harvest or soon thereafter. This is helpful for unloading the pollenizer plant and maintaining the flowering ability of the pollenizer plants for longer period of time. The brittle rind of the enhanced pollenizer also reduces the risk of carry-over into the next season, as a weed, since the fruit, and plant debris can be easily destroyed, after harvest of the triploid fruit.

Enhanced pollenizer plants flower about 7 days earlier than diploid Sangria. Enhanced pollenizer plants produce more than twice many of branches compared to Sangria. This allows enhanced pollenizer plants to produce more male flowers, thereby reducing the number of pollenizer plants needed. The vine of enhanced pollenizer plant is much thinner than regular diploid plants. The leaf size and leaf-lobe size of enhanced pollenizer are much smaller than those of Sangria. All these make enhanced pollenizer much less competitive for light, water and fertilizer, compared to regular diploid watermelon.

Enhanced pollenizer plants are producing male flowers after the harvest of triploid seedless fruits. This gives the potential of having a second fruit set and multiple harvests of triploid seedless fruit with single planting. The male flowers open earlier in the morning compared to regular watermelons, especially in the cooler days.

Example 8

Eight triploid varieties (see table 4) are transplanted on two 80" beds and spaced 24" apart. These two beds are located in the center of our regular hybrid evaluation block. A diploid hybrid bed is placed in each side of the two trial beds to eliminate the pollination factor. About 90 plants are transplanted for each variety. Two days later, each triploid plot is divided into 2 sub-plots and the enhanced pollenizer SP1 plants of the present invention are inserted in one of the 2 sub-plots in the ratio of 3:1, for each of the 8 triploid varieties. This planting pattern allows 3260 triploid plants per acre. The 8 triploid varieties differ in fruit shape, size and maturity. About 10 weeks later, the first 30 fruits are non-selectively harvested from each sub-plot and are weighted using a digital scale. Data are analyzed using S-Plus 6.1.

As shown in table 4, the fruit size differences are solely due to triploid variety differences. Inserting of enhanced pollenizer SP1 between regularly spaced triploid plants in the ratio of 3:1 does not reduce the fruit size of triploid seedless fruit, regardless of the type of triploid variety. The triploid varieties used in this trial represent a very broad spectrum of triploids used in commercial production. They differ in fruit size, fruit shape, and maturity. Thus, inserting enhanced pollenizer plants of the present invention between regularly spaced triploid plants does not reduce the fruit size of the triploid seedless melons. Therefore, a seedless grower can plant his or her fields solid with triploid plants and then insert the enhanced pollenizer plants in a ratio of 3:1 or less. This planting pattern and ratio allows growers to produce significant higher (25 to 33%) yields of seedless fruit per acre.

TABLE 3

Seedless Watermelon Fruit Yields Produced by Using Different Pollenizer and Rind Firmness of Different Pollenizer

| | Fruit/Plant | | | | Fruit/Acre | | | | Frt Wt (lbs) | | | | Rind Firmness |
| --- | --- | --- | --- | --- | --- | --- | --- | --- | --- | --- | --- | --- | --- |
| Pollinator | Palomar | RWT8124 | TriX313 | Mean | Palomar | RWT8124 | TriX313 | Mean | Palomar | RWT8124 | TriX313 | Mean | (g/mm$^2$) |
| SP Hyb 5:1 | 2.00 | 3.60 | 2.15 | 2.58 | 6534 | 11652 | 6957 | 8381 | 13.6 | 6.0 | 15.4 | 11.6 | NA |
| SP1 | 2.05 | 3.55 | 1.95 | 2.53 | 6719 | 11661 | 6413 | 8265 | 12.2 | 5.7 | 14.6 | 10.8 | 121 |
| SP1 x SP3 | 2.00 | 3.60 | 2.15 | 2.58 | 6579 | 11752 | 7001 | 8444 | 13.2 | 6.0 | 14.9 | 11.3 | 139 |
| SP2 | 1.90 | 3.50 | 1.90 | 2.43 | 6258 | 11479 | 6137 | 7958 | 12.1 | 6.0 | 13.3 | 10.5 | 123 |
| SP2 x SP1 | 1.85 | 3.30 | 2.20 | 2.45 | 6004 | 10728 | 7106 | 7946 | 13.1 | 5.8 | 14.0 | 10.9 | 129 |
| SP3 | 1.90 | 3.40 | 1.55 | 2.28 | 6210 | 11170 | 5116 | 7499 | 12.8 | 6.0 | 14.1 | 11.0 | 133 |
| SP3 x SP2 | 1.90 | 3.60 | 2.05 | 2.52 | 6219 | 11649 | 6577 | 8149 | 12.5 | 5.8 | 13.9 | 10.7 | 129 |
| Sangria 2:1 | 1.90 | 3.50 | 2.00 | 2.47 | 4086 | 7596 | 4375 | 5352 | 10.5 | 5.7 | 12.5 | 9.6 | |
| Sangria 3:1 | 1.95 | 3.35 | 1.95 | 2.42 | 4737 | 8248 | 4863 | 5949 | 12.4 | 5.6 | 12.9 | 10.3 | 302 |
| Mean | 1.95 | 3.52 | 2.02 | 2.49 | 5770 | 10405 | 5946 | 7374 | 12.5 | 5.8 | 13.8 | 10.7 | 154 |

| Factor | P-value | P-value | P-value | P-value |
| --- | --- | --- | --- | --- |
| Pollinator | 0.0239 | 0.0000 | 0.0000 | 0.0000 |
| Triploid | 0.0000 | 0.0000 | 0.0000 | |
| Pollinator*Triploid | 0.4121 | 0.0061 | 0.0029 | |
| Replication | 0.9372 | 0.8580 | 0.6310 | |

TABLE 4

Effect of Inserting Super-Pollenizer Between Regularly Spaced
(80" × 24") Triploid Plants in the Ratio of 3:1 to
the Fruit Size of Eight Different Triploid Watermelon Varieties

| Triploid Variety | Super-Pollenizer Insertion | | |
|---|---|---|---|
| | No | Yes | Mean |
| 3X Sangria | 18.05 | 18.51 | 18.28 |
| Palomar | 14.23 | 16.21 | 15.22 |
| RWT 8126 | 16.97 | 17.15 | 17.06 |
| RWT8124 | 6.26 | 6.03 | 6.15 |
| RWT8139 | 15.46 | 14.43 | 14.94 |
| RWT8140 | 15.31 | 15.73 | 15.52 |
| Shadow | 15.97 | 14.73 | 15.35 |
| Tri-X-313 | 15.77 | 15.60 | 15.69 |
| Mean | 14.75 | 14.80 | 14.77 |

| Factor | P-Value |
|---|---|
| Triploid Variety | 0.0000 |
| Super-Pollenizer | 0.8829 |
| Variety*Super-Pollenizer | 0.2451 |

DEPOSIT

Applicants have made a deposit of at least 2500 seeds of enhanced watermelon pollenizer line NO1F3203B (now called SP1) with the American Type Culture Collection (ATCC), Manassas, Va., 20110-2209 U.S.A., ATCC Deposit No: PTA-4856. This deposit of the enhanced watermelon pollenizer line NO1F3203B/SP1 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims. Thus, although the foregoing invention has been described in some detail in this document, it will be obvious that changes and modification may be practiced within the scope of the invention, as limited only by the scope of the appended claims.

All references cited herein are incorporated by reference in the application in their entireties.

What is claimed is:

1. A method for producing triploid, seedless watermelon fruit comprising the steps of:
    a) planting a field with rows of triploid watermelon plants;
    b) inter-planting diploid pollenizer watermelon plants comprising a gene e within said rows of triploid watermelon plants after every $2^{nd}$, $3^{rd}$, $4^{th}$, $5^{th}$, $6^{th}$, $7^{th}$, $8^{th}$, $9^{th}$, or $10^{th}$ triploid plants, wherein said diploid pollenizer watermelon plants are homozygous for said gene e;
    c) harvesting said triploid, seedless watermelon fruit.

2. A method for producing triploid, seedless watermelon fruit comprising the steps of:
    a) planting a field with rows of triploid watermelon plants;
    b) planting said field with rows of diploid watermelon plants comprising a gene e, wherein said diploid pollenizer watermelon plants are homozygous for said gene e, wherein the rows of diploid watermelon plants are approximately one-third to two-third the width of the rows of triploid watermelon plants.

3. The method for producing triploid, seedless watermelon fruit according to claim 2, wherein the rows of diploid watermelon plants are approximately one-half to two-thirds the width of the rows of triploid watermelon plants.

4. The method for producing triploid, seedless watermelon fruit according to claim 2, wherein said rows of diploid watermelon plants are planted after every two rows of triploid watermelon plants.

5. The method for producing triploid, seedless watermelon fruit according to claim 2, wherein said rows of diploid watermelon plants are planted after every three rows of triploid watermelon plants.

6. The method for producing triploid, seedless watermelon fruit according to claim 2, wherein said rows of diploid watermelon plants are planted after every four rows of triploid watermelon plants.

7. A method for producing triploid, seedless watermelon fruit, wherein the method comprises the steps of:
    a) interplanting a diploid watermelon plant comprising a gene e and triploid watermelon plants in a field, wherein said diploid pollenizer watermelon plant is homozygous for said gene e; and
    b) allowing pollination of said triploid watermelon plants by pollen of said diploid watermelon plant to obtain triploid, seedless watermelon fruit.

8. The method for producing triploid, seedless watermelon fruit according to claim 7, further comprising harvesting said triploid, seedless watermelon fruit.

9. The method for producing triploid, seedless watermelon fruit according to claim 2, wherein the rows of diploid watermelon plants are approximately one-third to one-half the width of the rows of triploid watermelon plants.

10. The method for producing triploid, seedless watermelon fruit according to claim 2, further comprising harvesting said triploid, seedless watermelon fruit.

11. A method of increasing the yield of triploid, seedless watermelon plants, wherein the method comprises the steps of:
    a) obtaining a diploid watermelon plant comprising a gene e, wherein said diploid pollenizer watermelon plants is homozygous for said gene e;
    b) planting said diploid watermelon plant in a field of triploid watermelon plants;
    c) allowing pollination of said triploid watermelon plants by pollen of said diploid watermelon plant to obtain triploid, seedless watermelon fruit; and
    d) harvesting said triploid, seedless watermelon fruit.

12. The method of increasing the yield of triploid, seedless watermelon plants according to claim 11, wherein planting of said diploid watermelon plant is at a ratio of approximately equal to or less than 1 diploid watermelon plant to 2 triploid, seedless watermelon plants.

13. The method of increasing the yield of triploid, seedless watermelon plants according to claim 11, wherein planting of said diploid watermelon plant is at a ratio of approximately equal to or less than 1 diploid watermelon plant to 4 triploid, seedless watermelon plants.

14. A method for producing triploid, seedless watermelon fruit, wherein the method comprises the steps of:
   a) interplanting seeds of a diploid watermelon plant comprising a gene e and triploid watermelon plants in a field, wherein said diploid pollenizer watermelon plant is homozygous for said gene e;
   b) allowing said seeds to grow into diploid watermelon plants; and
   c) allowing pollination of said triploid watermelon plants by pollen of said diploid watermelon plants to obtain triploid, seedless watermelon fruit.

15. The method for producing triploid, seedless watermelon fruit according to claim 14, further comprising harvesting said triploid, seedless watermelon fruit.

16. A method for producing triploid, seedless watermelon fruit, wherein the method comprises the steps of
   a) interplanting a diploid watermelon plant comprising a gene e and seeds of triploid watermelon plants in a field, wherein said diploid pollenizer watermelon plants is homozygous for said gene e;
   b) allowing said seeds to grow into triploid watermelon plants; and
   c) allowing pollination of said triploid watermelon plants by pollen of said diploid watermelon plant to obtain triploid, seedless watermelon fruit.

17. The method for producing triploid, seedless watermelon fruit according to claim 16, further comprising harvesting said triploid, seedless watermelon fruit.

18. A method for producing triploid, seedless watermelon fruit, wherein the method comprises the steps of
   a) interplanting seeds of a diploid watermelon plant comprising a gene e and seeds of triploid watermelon plants in a field, wherein said diploid pollenizer watermelon plant is homozygous for said gene e;
   b) allowing said seeds to grow into diploid watermelon plants and triploid watermelon plants, respectively; and
   c) allowing pollination of said triploid watermelon plants by pollen of said diploid watermelon plants to obtain triploid, seedless watermelon fruit.

19. The method for producing triploid, seedless watermelon fruit according to claim 18, further comprising harvesting said triploid, seedless watermelon fruit.

* * * * *